United States Patent
Bryant et al.

(10) Patent No.: US 8,764,414 B2
(45) Date of Patent: Jul. 1, 2014

(54) SYSTEM FOR DETECTING CONTAMINANTS IN AN INTAKE FLOW OF A COMPRESSOR

(75) Inventors: Paul Sherwood Bryant, Amesbury (GB); Julio Enrique Mestroni, Marietta, GA (US)

(73) Assignee: BHA Altair, LLC, Franklin, TN (US)

(*) Notice: Subject to any disclaimer, the term of this patent is extended or adjusted under 35 U.S.C. 154(b) by 192 days.

(21) Appl. No.: 13/290,849

(22) Filed: Nov. 7, 2011

(65) Prior Publication Data

US 2013/0115114 A1 May 9, 2013

(51) Int. Cl.
*F04D 25/04* (2006.01)
*F04C 28/00* (2006.01)
*G01N 25/02* (2006.01)
*F02M 35/08* (2006.01)
*F02C 7/04* (2006.01)
*G01N 25/68* (2006.01)
*F01D 17/08* (2006.01)

(52) U.S. Cl.
CPC ............. *G01N 25/68* (2013.01); *F02M 35/088* (2013.01); *F05D 2260/80* (2013.01); *F02C 7/04* (2013.01); *Y02T 10/166* (2013.01); *F01D 17/08* (2013.01)
USPC .............. 417/282; 417/405; 417/406; 374/19

(58) Field of Classification Search
USPC .......................... 417/279, 282, 375, 405–407; 374/16–20
See application file for complete search history.

(56) References Cited

U.S. PATENT DOCUMENTS

| | | | |
|---|---|---|---|
| 3,166,928 A * | 1/1965 | Jackson et al. | 374/20 |
| 4,345,455 A * | 8/1982 | Hayes, Jr. | 374/20 |
| 4,554,793 A * | 11/1985 | Harding, Jr. | 62/126 |
| 4,799,235 A | 1/1989 | Bannell | |
| 5,022,045 A * | 6/1991 | Elliott | 374/20 |
| 5,052,818 A * | 10/1991 | Nishizawa et al. | 374/17 |
| 5,353,585 A * | 10/1994 | Munk | 60/775 |
| 5,460,450 A | 10/1995 | Buck | |
| 5,852,398 A | 12/1998 | Helman | |
| 6,575,621 B1 * | 6/2003 | Zlochin | 374/28 |
| 6,715,916 B2 * | 4/2004 | Tomlinson et al. | 374/144 |
| 6,817,197 B1 | 11/2004 | Padfield | |
| 6,842,018 B2 | 1/2005 | McIntosh | |
| 6,926,439 B2 * | 8/2005 | Zlochin | 374/20 |
| 7,380,980 B2 * | 6/2008 | Kanai et al. | 374/19 |
| 7,581,877 B1 * | 9/2009 | Zarrabian | 374/16 |
| 7,645,322 B2 * | 1/2010 | Olsen et al. | 95/14 |
| 2001/0035150 A1 | 11/2001 | Daly | |
| 2007/0239344 A1 | 10/2007 | Durand | |
| 2011/0052377 A1 * | 3/2011 | Chamoto et al. | 415/180 |

OTHER PUBLICATIONS

Search Report and Written Opinion from corresponding EP Application No. 12191616, dated Apr. 19, 2013.

* cited by examiner

*Primary Examiner* — Peter J Bertheaud
(74) *Attorney, Agent, or Firm* — Reinhart Boerner Van Deuren s.c.

(57) ABSTRACT

A system includes a detector configured to detect a fog condition within an air flow directed toward a compressor. The system also includes a controller coupled to the detector, wherein the controller is configured to activate a first control measure in response to the fog condition.

17 Claims, 3 Drawing Sheets

SYSTEM FOR DETECTING CONTAMINANTS IN AN INTAKE FLOW OF A COMPRESSOR

BACKGROUND OF THE INVENTION

The subject matter disclosed herein relates to a system for detecting contaminants (e.g., fog and/or dust) in an intake flow of a compressor such as a gas turbine compressor.

In general, gas turbine engines combust a mixture of compressed air and fuel to produce hot combustion gases. The combustion gases may flow through a turbine to generate power for a load and/or a compressor. As will be appreciated, contaminants (e.g., fog and/or dust conditions) at the gas turbine inlet may adversely affect a filtration system located within the gas turbine inlet upstream of the compressor. In particular, fog and/or dust conditions may result in excessive pressure loss within the gas turbine system, thus, impacting system performance. Typically, fog and/or dust conditions may be only visually identified at the gas turbine inlet or predicted based on a historical basis. Thus, in order to combat the fog and/or dust conditions, the gas turbine inlets may be fitted full time with coalescers. However, the full time fitment of coalescers adversely impacts the differential pressure within the gas turbine inlet. In addition, the full time fitment of coalescers involves additional maintenance requirements and increases operational costs.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In accordance with a first embodiment, a system includes a detector configured to detect a fog condition within an air flow directed toward a compressor. The system also includes a controller coupled to the detector, wherein the controller is configured to activate a first control measure in response to the fog condition.

In accordance with a second embodiment, a system includes a compressor intake configured to provide an air flow to a compressor of a gas turbine. The system also includes at least one filter disposed within the turbine compressor intake. The system further includes a detector disposed at an angle relative to a direction of the air flow, wherein the detector is configured to detect a fog condition within the air flow. The system yet further includes a controller coupled to the detector, wherein the controller is configured to activate a first control measure in response to the fog condition.

In accordance with a third embodiment, a system includes a compressor intake contaminant detector configured to monitor an air flow into a compressor of a gas turbine, wherein the compressor intake contaminant detector is configured to detect a fog condition or a dust condition within the air flow.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
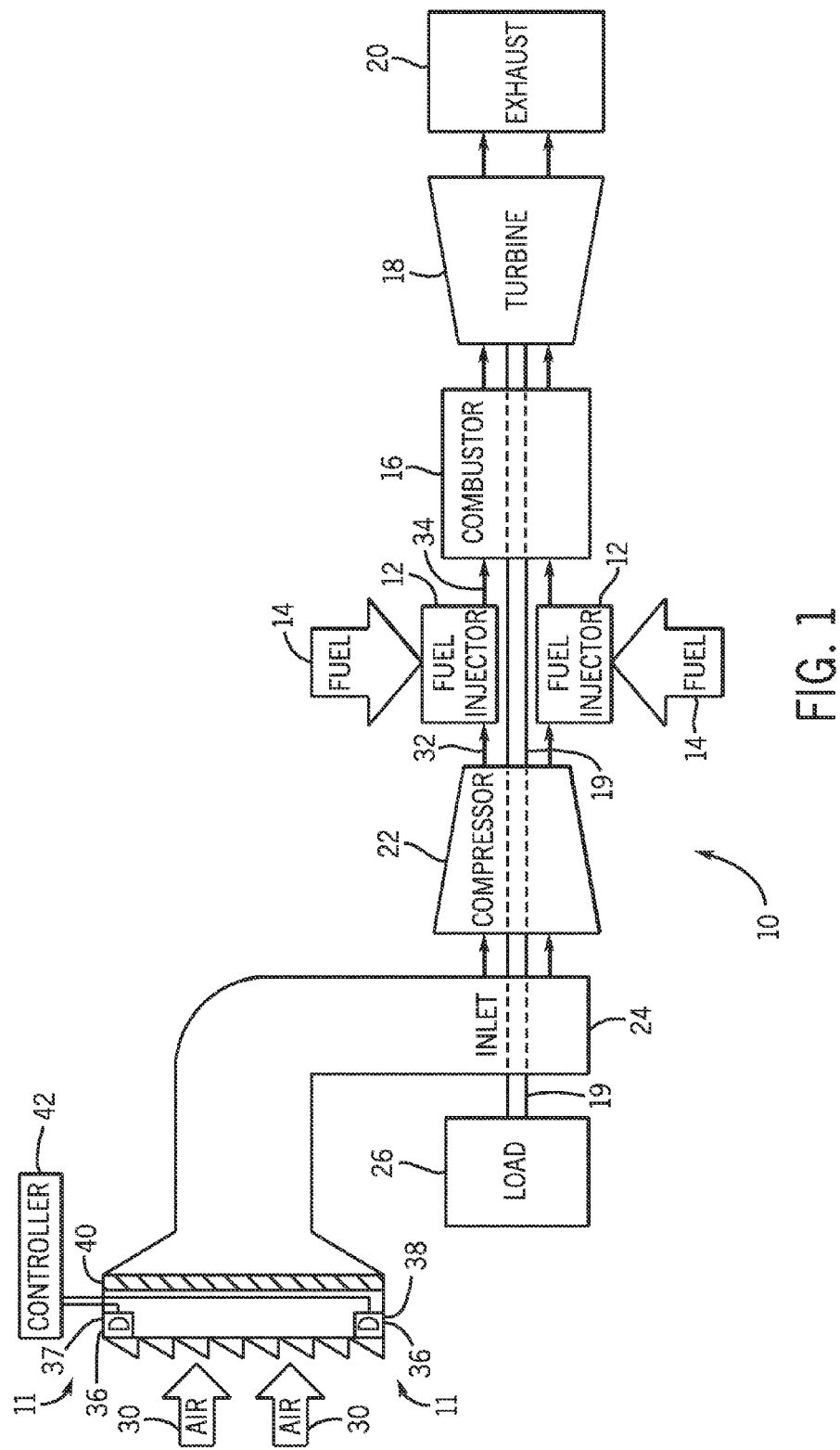
FIG. 1 is a block diagram of an embodiment of a gas turbine system including a contaminant detection system configured to detect contaminants (e.g., fog and/or dust conditions) within an air flow of a turbine air intake directed into a compressor of the gas turbine system.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure include a system to detect contaminants (e.g., fog and/or dust conditions) within a turbine air intake that directs air flow to a compressor. For example, certain embodiments include a detector (e.g., contaminant detector) directed toward an air flow into a compressor, wherein the detector is configured to detect contaminants within the air flow (e.g., fog and/or dust conditions). In addition, a controller is coupled to the detector and configured to activate control measures (e.g., active coalescers) in response to fog and/or dust conditions. In certain embodiments, the controller may provide a signal output that a fog and/or dust condition is occurring upon which other devices can action a response (e.g., external control or data gathering). In order to detect a fog condition (i.e., presence of condensed water vapor in air that forms cloud near ground), the detector may include a chilled mirror hygrometer and a laser detection system to measure a dew point within the air flow. For example, the chilled mirror hygrometer may include a plate (e.g., transparent medium) with a polished surface coupled to a pulse-width modulation controlled thermoelectric device (e.g., Peltier device), where the thermoelectric device adjusts the temperature of the plate to form a cloud due to condensation on the plate. In addition, in order to detect a fog condition, the detector may include an electronic sensor configured to detect condensation on the plate. For example, the electronic sensor may include an internal refraction device configured to emit light at the plate at an angle and to receive refracted light from moisture located on the plate. Further, in order to detect the dust condition (i.e., the presence of dust such as from a dust storm) within the air flow, the plate of the detector may include a gutter to collect water and the detector may include a sensor configured to measure the salt content within the collected water. In certain embodiments, the system may include a plurality of detectors. The detection system enables accurate data related to the fog and/or dust conditions to be gathered for specific sites. For example, the controller is configured to collect data from the detector related to the occurrence of the fog and/or the dust conditions. In addition, the detection system enables the use of active controls to protect the gas turbine inlet from fog and/or dust conditions. Therefore, the detection system reduces the need for full time fitment of coalescers (e.g., mechanical coalescers with coalescing filters configured to remove contaminants from the air flow) within the gas turbine inlet and, thus, reduces maintenance requirements, operational costs, and differential pressure (dP) impact associated with the full time fitment of coalescers.

Turning now to the drawings, FIG. 1 is a block diagram of a turbine system 10 including a contaminant detection system 11 (e.g., compressor intake contaminant system or fog and detection system) configured to detect contaminants (e.g., fog and/or dust conditions) within an air flow of a turbine air intake (e.g., turbine compressor intake) directed into a compressor. The turbine system 10 is described below for the purpose of providing context for embodiments of the present contaminant detection system 11. It should be appreciated that the contaminate detection system 11 described below may be utilized for detecting fog and/or dust conditions of air flows into other compressors, such as those used in air separation plants, blast furnaces, or other applications employing compressed air.

In the present embodiment, the turbine system 10 (e.g., gas turbine engine) includes a fuel injector 12, a fuel supply 14, and a combustor 16. As illustrated, the fuel supply 14 routes a liquid fuel and/or gas fuel, such as natural gas, to the gas turbine system 10 through the fuel injector 12 into the combustor 16. As discussed below, the fuel injector 12 is configured to inject and mix the fuel with compressed air. The combustor 16 ignites and combusts the fuel-air mixture, and then passes hot pressurized exhaust gas into a turbine 18. As will be appreciated, the turbine 18 includes one or more stators having fixed vanes or blades, and one or more rotors having blades which rotate relative to the stators. The exhaust gas passes through the turbine rotor blades, thereby driving the turbine rotor to rotate. Coupling between the turbine rotor and a shaft 19 will cause the rotation of the shaft 19, which is also coupled to several components throughout the gas turbine system 10, as illustrated. Eventually, the exhaust of the combustion process may exit the gas turbine system 10 via an exhaust outlet 20.

A compressor 22 includes blades rigidly mounted to a rotor which is driven to rotate by the shaft 19. As air passes through the rotating blades, air pressure increases, thereby providing the combustor 16 with sufficient air for proper combustion. The compressor 22 may intake air to the gas turbine system 10 via an inlet 24 (e.g., turbine air intake or turbine compressor intake). Further, the shaft 19 may be coupled to a load 26, which may be powered via rotation of the shaft 19. As will be appreciated, the load 26 may be any suitable device that may use the power of the rotational output of the gas turbine system 10, such as a power generation plant or an external mechanical load. For example, the load 26 may include an electrical generator, a propeller of an airplane, and so forth.

The inlet 24 draws air 30 into the gas turbine system 10. The air 30 then flows through blades of the compressor 22, which provides compressed air 32 to the combustor 16. In particular, the fuel injector 12 may inject the compressed air 32 and fuel 14, as a fuel-air mixture 34, into the combustor 16. Alternatively, the compressed air 32 and fuel 14 may be injected directly into the combustor for mixing and combustion.

As illustrated, the turbine system 10 includes the contaminant detection system 11 configured to detect contaminants such as fog and/or dust conditions (e.g., from dust storms) within an air flow of the inlet 24 directed into the compressor 22. In the present embodiment, the fog and dust detection system 11 includes a detector 36 (e.g., compressor intake contaminant detector) disposed upstream of a filtration system 40 and directed toward an air flow through the gas turbine inlet 24. In certain embodiments, the detector 36 (e.g., a plate of the detector 36) may be disposed at an angle relative to a direction of air flow 52 within the inlet 24. As illustrated, the contaminant detection system 11 may include a plurality of detectors 36 (e.g., detectors 37, 38). The number of detectors 36 may vary from 1 to 20 or more. The detector 36 is configured to detect fog and/or dust conditions within the air flow. For example, to detect fog conditions, the detector 36 may include a chilled mirror hygrometer and a laser detection system (e.g., light-emitting diode (LED) detection system) to measure a dew point within the air flow. In addition, detector 36 may include an electronic sensor (e.g., internal refraction device) configured to detect condensation on a transparent medium or plate (e.g., glass or plastic). The detector 36 may also include a sensor to measure temperature within the air flow. The contaminant detection system 11 includes a controller 42 coupled (e.g., communicatively coupled) to the detector 36. The detector 36 is configured to generate a signal indicative of a fog condition based on the dew point, detected condensation, and/or temperature and provide the signal to the controller 42. To detect dust conditions within the air flow, the detector 36 may collect water (e.g., via at least one gutter disposed in the plate) and a sensor (e.g., salt sensor) configured to measure a salt content within the collected water (e.g., via a resistance measurement). The detector 36 is also configured to generate a signal indicative of a fog condition based on the salt content within the collected water and provide the signal to the controller 42.

The controller 42 may control the operation of the other components of the contaminant detection system 11. For example, the controller 42 may control the angle of the plate of the detector 36, the chilled mirror hygrometer operation, the laser detection system operation, the electronic sensor (e.g., internal refraction device) operation, and/or the salt sensor operation. In addition, the controller 42 is configured to activate control measurements in response to the signals indicative of fog and/or dust conditions. For example, the controller 42 may activate the use of active coalescers (e.g., mechanical coalescers with coalescing filters configured to remove contaminants such steam and dust from the air flow), internal and/or external, or other control measures in the inlet 24 in response to fog and/or dust conditions. In addition, the detection system 11 enables accurate data related to the fog and/or dust conditions to be gathered for specific installation sites of gas turbine engines or other compressors. Also, via the active control measures, the detection system 11 protects the gas turbine inlet 24 from fog and/or dust conditions. Further, the detection system 11 reduces the need for full time fitment of coalescers within the gas turbine inlet 24 and, thus, reduces maintenance requirements, operational costs, and dP impact associated with the full time fitment of coalescers.

Figure 2:
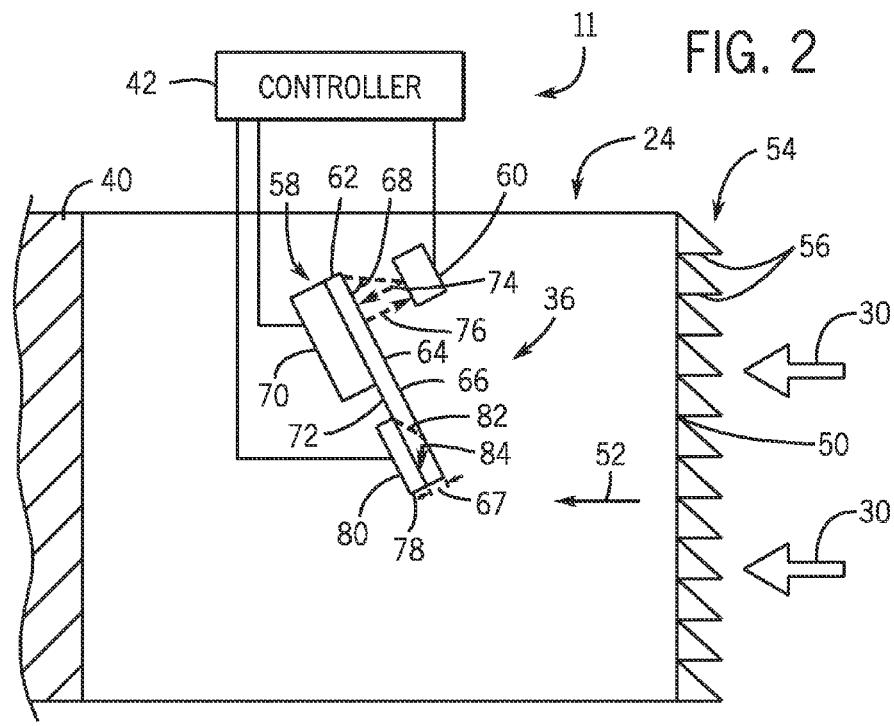
FIG. 2 is a schematic of an embodiment of a turbine air intake configured to provide an air flow to the compressor having a contaminant detector (e.g., fog)

FIG. 2 is a schematic of an embodiment of the turbine air intake or turbine compressor intake 24 configured to provide an air flow to the compressor 22. As illustrated, air 30 enters an air inlet 50 of the turbine air intake 24 and flows toward the compressor 22 along a downstream direction 52. In the present embodiment, the air enters the air inlet 50 of the turbine air intake 24 through a weather hood 54. As will be appreciated, the weather hood 54 includes a series of slats 56 configured to deflect rain drops, sleet and/or snow away from the turbine air intake 24, thereby substantially reducing the moisture content of the incoming air. The air flow then passes through a filter assembly 40 (e.g., including at least one filter) that removes dirt and/or other debris which may otherwise enter the gas turbine system 10. The filter assembly 40 is disposed within the turbine air intake 24 downstream of the air inlet 50.

The turbine air intake 24 includes the contaminant detection system 11 to detect fog and/or dust conditions. The fog and detection system 11 includes the detector 36 (e.g., fog and dust detector) disposed within the turbine air intake 24. Specifically, the detector 36 is directed toward the air flow into the turbine air intake 24 and, thus, the compressor 22. The detector 36 includes a chilled mirror hygrometer 58 and a laser detection system 60 (e.g., LED detection system), which together are configured to measure a dew point (and thus water vapor content) within the air flow. The chilled mirror hygrometer 58 includes a plate 62 (e.g., mirror) with a reflective surface 64 on a front side 66 of the plate 62 facing the air flow. The reflective surface 64 may extend over the entire front side 66 of the plate 62 or only a portion of the front side 66. The plate 62 may be composed of a transparent medium such as glass or plastic. A thickness 67 of the plate 62 may range from approximately 1 to 2 mm or any other thickness 67. In addition, the plate 62 (and, thus, the detector 36) is disposed at an angle 68 relative to the direction of air flow 52 between the air inlet 50 and the filter assembly 40. The angle 68 may range from approximately 25 to 90 degrees, 25 to 45 degrees, 45 to 60 degrees, 60 to 90 degrees, and any other range that effectively measures the air 30. For example, the angle 68 may be approximately 25, 30, 35, 40, 45, 50, 55, 60, 65, 70, 75, 80, 85, or 90 degrees, or any other angle. The chilled mirror hygrometer 58 also includes a pulse-width modulation (PWM) controlled thermoelectric device 70 coupled to a backside 72 of the plate 62. The thermoelectric device 70 is configured to adjust a temperature of the plate 62 to condense a cloud of water on the plate 62. The laser detection system 60 emits a light or a laser 74 (e.g., from a light emitting diode (LED) or other type of light source) towards the reflective surface 64 of the plate 62. The laser detection system 60 includes a photodetector that monitors light 76 reflected from the polished surface 64 back towards the system 60. Dew droplets on the polished surface 64 scatter the reflected light 76 and the amount of light 76 detected by the photodector. In fog conditions, larger quantities of water may condense on the cooled surface 64 of the chilled mirror hygrometer 58.

The detector 36 also includes an electronic sensor 78 configured to detect condensation on the transparent plate 66. The electronic sensor 78 is coupled to the backside 72 of the plate 62. In particular, the electronic sensor 74 includes an internal refraction device 80 configured to emit light 82 (e.g., infrared light) at the transparent plate 62 at an angle (e.g., approximately 45 degrees) and to receive light 84 refracted from moisture located on the front side 66 of the plate 62 to detect condensation on the plate 62. In certain embodiments, the detector 36 may also include a temperature sensor.

The chilled hygrometer 58, laser detection system 60, and the electronic sensor 78 are coupled (e.g., communicatively coupled) to the controller 42. The controller 42 may control these components of the detector 36. For example, the controller 42 may adjust the angle 68 of the plate 62, operation of the chilled mirror hygrometer 58, operation of the laser detection system 60, and operation of the electronic sensor 78. The controller 42 also receives signals indicative of a fog condition from these components of the detector 36. Based on the dew point, detected condensation, and/or temperature, the controller 42 may determine the presence of a fog condition and activate control measures in response to the fog condition. For example, the controller 42 may activate active coalescers (e.g., internal and/or external) or other control measures in the turbine air intake 24 to counteract the fog conditions. The detection system 11 enables accurate data related to the fog conditions to be gathered for specific installation sites of gas turbine engines or other compressors. Also, via the active control measures, the detection system 11 protects the turbine air intake 24 (e.g., turbine compressor intake) from fog conditions. Further, the detection system 11 reduces the need for full time fitment of coalescers within the turbine air intake 24 and, thus, reduces maintenance requirements, operational costs, and dP impact associated with the full time fitment of coalescers.

Figure 3:
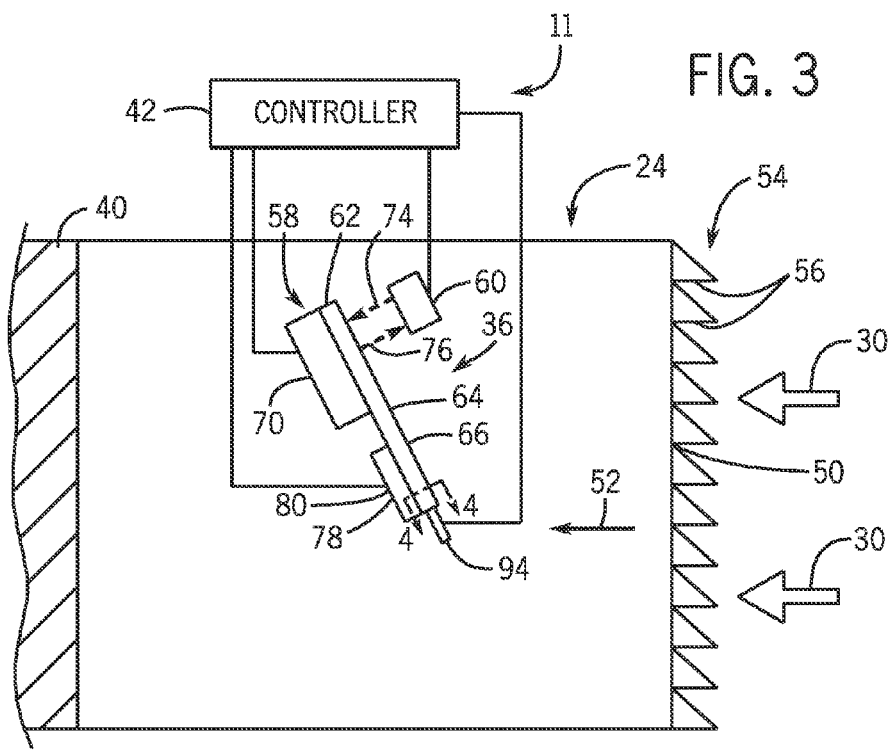
FIG. 3 is a schematic of an embodiment of a turbine air intake configured to provide an air flow to the compressor having a contaminant detector (e.g. fog and dust)

As mentioned above, the detection system 11 may also detect dust conditions. FIG. 3 is a schematic of an embodiment of the turbine air intake 24 configured to provide an air flow to the compressor 22 and having the detection system 11. The turbine air intake 24 and detection system 11 are as described in FIG. 3. In addition, the detector 36 includes a sensor 94 (e.g., salt sensor) configured to measure a salt content of water collected by the plate 62. The salt content of the water may be indicative of a dust condition (e.g., dust storms) and/or the salt content in intake air fog. Water may be collected from the plate 62 of the detector 36 via one or more gutters disposed on the plate 62 (see FIG. 4). The sensor 94 may determine the presence of salt within the collected water via a resistance measurement. The sensor 94 is also coupled to the controller 42. The controller 42 may control the operation of the sensor 94. In addition, the controller 42 receives a signal indicative (e.g., resistance measurement of collected water) of a dust condition form the sensor 94. Based on the resistance measurement of the collected water, the controller 42 may determine the presence of a dust condition and activate control measures in response to the dust condition. For example, the controller 42 may activate active coalescers (e.g., internal and/or external) or other control measures in the turbine air intake 24 to counteract the dust condition. The detection system 11 enables accurate data related to the dust conditions to be gathered for specific installation sites of gas turbine engines or other compressors. Also, via the active control measures, the detection system 11 protects the turbine air intake 24 from dust conditions. Further, the detection system 11 reduces the need for full time fitment of coalescers within the turbine air intake 24 and, thus, reduces maintenance requirements, operational costs, and dP impact associated with the full time fitment of coalescers.

Figure 4:
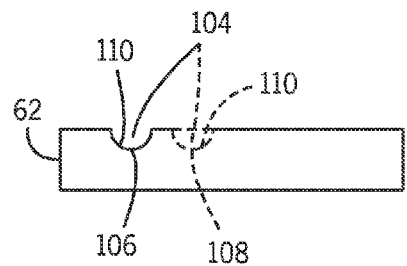
FIG. 4 is a cross-sectional view of an embodiment of a plate of the contaminant detector of FIG. 3, taken along line 4-4.

FIG. 4 is a cross-sectional view of an embodiment of the plate 62 of the fog and dust detector 36 of FIG. 3, taken along line 4-4. The plate 62 includes one or more gutters 104 (e.g., gutters 106 and 108) that run lengthwise along the plate 62. The number of gutters 104 on the plate 62 may range from 1 to 10 or any other suitable number. In certain embodiments, the gutter 104 may run for an entire length of the plate 62 or a portion of the length of the plate 62. As illustrated, the gutter 104 includes a concave recess 110. In certain embodiments, the shape of the recess 110 may vary. For example, the recess 110 may be rectilinear, triangular, or any other shape. The gutter 104 is configured to collect water for the sensor 94. The angle 68 of the plate 62 enables the collected water to flow along the gutter 104 via gravity to the sensor 94.

Figure 5:
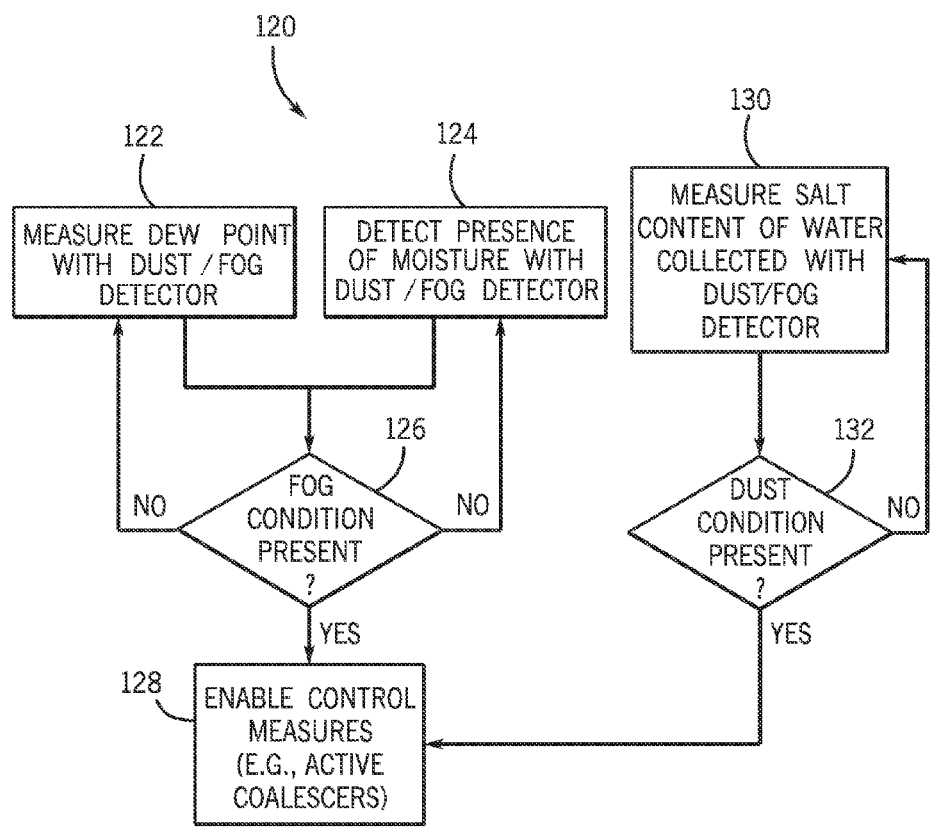
FIG. 5 is a flowchart of an embodiment of a method for detecting contaminant conditions (e.g., fog and dust conditions) within a turbine air intake.

FIG. 5 is a flowchart of an embodiment of a method 120 for detecting fog and dust conditions within the turbine air intake 24 utilizing the embodiments of the detection system 11 described above. The method 120 includes measuring a dew point with the detector 36 (block 122). For example, the detector 36 may utilize the chilled mirror hygrometer 58 and laser detection system 60 described above to obtain the dew point. The method 120 also includes detecting the presence of moisture with the detector (block 124). For example, the detector 36 may measure the internal refraction of light (e.g., infrared light) by moisture present on the transparent plate 62 via the electronic sensor 78 (e.g., internal refraction device 80) as described above. The dew point and/or detected moisture are provided to the controller 42 to determine whether a fog condition exists (block 126). If a fog condition does not exist, the detection system 11 continues measuring the dew point (block 122) and detecting the presence of moisture (block 124) with the detector 36. If a fog condition is present, then the controller 42 enables or activates control measures (e.g., a first control measure) (block 128). For example, the controller 42 may activate active coalescers internal and/or external to the turbine air intake 24 as the first control measure.

In addition to monitoring for a fog condition, the method 120 includes monitoring for a dust condition. The method 120 includes measuring a salt content within collected water (e.g., via a resistance measurement) using the sensor 94 (e.g., salt sensor) of the detector 36 (block 130) as describe above. The measurement for salt content within the collected water is provided to the controller 42 to determine whether a dust condition exists (block 132). If a dust condition does not exist, the detection system 11 continues measuring the salt content of the collected water (block 130). If a dust condition is present, then the controller 42 enables or activates control measures (e.g., the first control measure or a second control measure) (block 128). For example, the controller 42 may activate active coalescers internal and/or external to the turbine air intake 24 as the first control measure. Alternatively, the controller 42 may activate a second control measure. For example, the second control measure may include providing a warning or alarm of the occurrence of salt condensation. In certain embodiments, the second control measure may generate a signal proportional to the salt content for inclusion in a database. The signal may also be used for comparative purposes. For example, a first sensor 94 may be disposed upstream of the filtration system 40 and a second sensor 94 disposed downstream of the filtration system to enable a comparison of the salt content representative signals to provide an indication of the efficiency of the filtration system 40.

Technical effects of the disclosed embodiments include systems for detecting the presence of contaminants (e.g., fog and/or dust conditions) within the turbine air intake 24 (e.g., turbine compressor intake). In particular, the detection system 11 includes one or more detectors 36 directed toward an air flow into the compressor 22. The one or more detectors 36 are configured to measure the dew point (e.g., via the chilled mirror hygrometer 58 and the laser detection system 60) and/or detect the presence of moisture (e.g., via the electronic sensor 80). In addition, the one or more detectors 36 are configured to measure the salt content of collected water (e.g., via the sensor 94). Based on signals indicative of fog and/or dust conditions from the detector 36, the controller 42 coupled to the detector 36 determines the presence of fog and/or dust conditions. In addition, the controller 42 activates control measures (e.g., active coalescers) in response to fog and/or dust conditions. The detection system 11 enables accurate data related to fog and/or dust conditions to be gathered for specific sites. Also, via the active control measures, the detection system 11 protects the turbine air intake 24 from fog and/or dust conditions. Further, the detection system 11 reduces the need for full time fitment of coalescers within the turbine air intake 24 and, thus, reduces maintenance requirements, operational costs, and dP impact associated with the full time fitment of coalescers.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system comprising:
a detector configured to detect a fog condition within an air flow directed toward a compressor, the detector defining a gutter configured to collect water from the detector and channel the water to a salt sensor, the salt sensor configured to detect salt content of the water, wherein the detector further comprises a chilled mirror hygrometer and a laser detection system configured to measure a dew point within the air flow; and
a controller coupled to the detector and salt sensor, wherein the controller is configured to activate a first control measure in response to the fog condition.

2. The system of claim 1, wherein the chilled mirror hygrometer comprises a plate with a reflective surface coupled to a pulse-width modulation controlled thermoelectric device, wherein the pulse-width modulation controlled thermoelectric device is configured to adjust a temperature of the plate to condense a cloud of water on the plate.

3. The system of claim 1, wherein the detector comprises an electronic sensor configured to detect condensation on a transparent plate.

4. The system of claim 3, wherein the electronic sensor comprises an internal refraction device configured to emit light at the transparent plate at an angle and to receive refracted light from moisture located on the transparent plate.

5. The system of claim 1, wherein the detector is configured to detect a dust condition within the air flow, and the controller is configured to activate the first control measure or a second control measure in response to the dust condition.

6. The system of claim 1, wherein the controller is configured to collect data from the detector related to the occurrence of the fog.

7. The system of claim 1, comprising the compressor or a gas turbine engine having the compressor.

8. The system of claim 1, wherein the first control measure comprises at least one active coalescer.

9. The system of claim 1, wherein the detector is configured to detect the fog condition based on a measured dew point and detected condensation.

10. A system comprising:
a compressor intake configured to provide an air flow to a compressor of a gas turbine;

at least one filter disposed within the turbine compressor intake;

a detector disposed at an angle relative to a direction of the air flow, wherein the detector is configured to detect a fog condition within the air flow, the detector defining a gutter configured to collect water from the detector and channel the water to a salt sensor, the salt sensor configured to detect salt content of the water, wherein the detector further comprises a chilled mirror hygrometer and a laser detection system configured to measure a dew point within the air flow; and a controller coupled to the detector and salt sensor, wherein the controller is configured to activate a first control measure in response to the fog condition.

11. The system of claim 10, wherein the detector comprises an electronic sensor configured to detect condensation on a transparent plate.

12. The system of claim 10, wherein the detector is configured to detect a dust condition within the air flow, and the controller is configured to activate the first control measure or a second control measure in response to the dust condition.

13. The system of claim 10, wherein the first control measure comprises at least one active coalescer.

14. The system of claim 10, wherein the system comprises a plurality of the detectors.

15. The system of claim 10, wherein the angle is approximately 25 to 90 degrees relative to the direction of the air flow.

16. A system, comprising:

a compressor intake contaminant detector configured to monitor an air flow into a compressor of a gas turbine, the contaminant detector includes a chilled mirror hygrometer and a separate salt sensor which measures the salt content of water, wherein the compressor intake contaminant detector is configured to detect a fog condition including presence of salt.

17. The system of claim 16, comprising a controller coupled to the compressor intake contaminant detector, wherein the controller is configured to activate at least one control measure in response to the fog condition.

* * * * *